(12) United States Patent
Sahatjian

(10) Patent No.: US 7,291,110 B2
(45) Date of Patent: Nov. 6, 2007

(54) CATHETER LESION DIAGNOSTICS

(75) Inventor: Ronald A. Sahatjian, Lexington, MA (US)

(73) Assignee: Boston Scientific Corporation, Natick, MA (US)

( * ) Notice: Subject to any disclaimer, the term of this patent is extended or adjusted under 35 U.S.C. 154(b) by 561 days.

(21) Appl. No.: 10/269,160

(22) Filed: Oct. 11, 2002

(65) Prior Publication Data

US 2003/0092977 A1  May 15, 2003

Related U.S. Application Data

(60) Provisional application No. 60/329,193, filed on Oct. 12, 2001.

(51) Int. Cl.
*A61B 8/00* (2006.01)
*A61B 8/12* (2006.01)

(52) U.S. Cl. .................. 600/439; 600/463; 600/466

(58) Field of Classification Search ............... 600/439, 600/462–471; 604/96.01, 264; 606/191, 606/194
See application file for complete search history.

(56) References Cited

U.S. PATENT DOCUMENTS

| | | | |
|---|---|---|---|
| 3,903,733 A | 9/1975 | Murayama et al. | |
| 4,566,465 A | 1/1986 | Arhan et al. | |
| 4,576,177 A | 3/1986 | Webster, Jr. | |
| 4,600,855 A | 7/1986 | Strachan | |
| 4,809,710 A | 3/1989 | Williamson | |
| 4,815,472 A | 3/1989 | Wise et al. | |
| 4,843,275 A | 6/1989 | Radice | |
| 4,873,990 A | 10/1989 | Holmes et al. | |
| 4,949,729 A | 8/1990 | Haski | |
| 5,050,609 A | 9/1991 | Balaban et al. | |
| 5,117,840 A | 6/1992 | Brenman et al. | |
| 5,135,001 A * | 8/1992 | Sinofsky et al. | 600/459 |
| 5,141,518 A * | 8/1992 | Hess et al. | 606/194 |
| 5,195,969 A * | 3/1993 | Wang et al. | 604/96.01 |
| 5,306,246 A * | 4/1994 | Sahatjian et al. | 604/96.01 |
| 5,353,798 A | 10/1994 | Sieben | |
| 5,396,887 A | 3/1995 | Imran | |
| 5,443,495 A | 8/1995 | Buscemi et al. | |
| 5,483,163 A | 1/1996 | Wen et al. | |
| 5,496,311 A * | 3/1996 | Abele et al. | 606/28 |
| 5,588,432 A * | 12/1996 | Crowley | 600/439 |
| 5,609,606 A * | 3/1997 | O'Boyle | 606/194 |
| 5,611,807 A | 3/1997 | O'Boyle | |
| 5,685,311 A | 11/1997 | Hara | |
| 5,741,229 A | 4/1998 | Robinson et al. | |
| 5,797,877 A * | 8/1998 | Hamilton et al. | 604/96.01 |
| 5,840,031 A | 11/1998 | Crowley | |
| 5,846,218 A * | 12/1998 | Brisken et al. | 604/22 |

(Continued)

FOREIGN PATENT DOCUMENTS

JP   3-274899   3/1991

(Continued)

OTHER PUBLICATIONS

International Search Report.

(Continued)

*Primary Examiner*—Francis J. Jaworski
(74) *Attorney, Agent, or Firm*—Fish & Richardson P.C.

(57) ABSTRACT

Catheter lesion diagnostics are disclosed.

26 Claims, 4 Drawing Sheets

U.S. PATENT DOCUMENTS

| | | | |
|---|---|---|---|
| 5,848,969 A * | 12/1998 | Panescu et al. | 600/462 |
| 5,865,801 A * | 2/1999 | Houser | 604/103.07 |
| 5,871,449 A | 2/1999 | Brown | |
| 5,954,706 A | 9/1999 | Sahatjian | |
| 5,957,950 A * | 9/1999 | Mockros et al. | 606/194 |
| 6,019,727 A | 2/2000 | Koger et al. | |
| 6,023,632 A * | 2/2000 | Wilk | 600/407 |
| 6,036,647 A | 3/2000 | Suorsa et al. | |
| 6,074,407 A * | 6/2000 | Levine et al. | 606/194 |
| 6,083,170 A | 7/2000 | Ben-Haim | |
| 6,200,268 B1 | 3/2001 | Vince et al. | |
| 6,217,518 B1 | 4/2001 | Holdaway et al. | |
| 6,231,520 B1 | 5/2001 | Maezawa | |
| 6,245,026 B1 | 6/2001 | Campbell et al. | |
| 6,248,083 B1 | 6/2001 | Smith et al. | |
| 6,261,237 B1 | 7/2001 | Swanson et al. | |
| 6,425,877 B1 * | 7/2002 | Edwards | 604/21 |
| 6,427,089 B1 * | 7/2002 | Knowlton | 607/101 |
| 6,514,249 B1 * | 2/2003 | Maguire et al. | 606/41 |
| 6,615,071 B1 * | 9/2003 | Casscells et al. | 600/474 |
| 6,689,156 B1 * | 2/2004 | Davidson et al. | 623/1.11 |
| 6,811,544 B2 * | 11/2004 | Schaer | 604/95.04 |
| 6,896,842 B1 * | 5/2005 | Hamilton et al. | 254/515 |
| 6,946,092 B1 | 9/2005 | Bertolino et al. | |
| 2002/0165523 A1 | 11/2002 | Chin et al. | |
| 2005/0148997 A1 | 7/2005 | Valley et al. | |

FOREIGN PATENT DOCUMENTS

| | | |
|---|---|---|
| JP | 10-43142 | 10/1998 |
| WO | WO99/58059 A | 11/1999 |

OTHER PUBLICATIONS

Chang, Fu-Kuo et al., "Diagnostic Layer and Methods for Detecting Structural Integrity of Composite and Metallic Materials," *J. Accoust. Soc. Am.*, vol. 112, No. 5, Pt. 1, Nov. 2002. p. 1736.

Dugnani, Roberto et al., "A Novel Impedance-based Sensor Technique for Real Time, in vivo, Unstable Plaque Characterization," First European Workshop on Strucural Health Monitoring.

Gaunt, M.E. et al., "Unstable Carotid Plaques: Preoperative Identification and Association with Intraoperative Embolisation Detected by Transcranial Doppler," *Eur J. Vasc. Endovasc Surg*, Jan. 1996; 11(1):78-82.

Helft, G. et al., "(article in French)", *Arch Mal Coeur Vaiss* Jun. 2001 94(6):583-90.

Hiro, T. et al., "Detection of Fibrous Cap in Atherosclerotic Plaque by Intravascular Ultrasound by Use of Color Mapping of Angle-Dependent Echo-Intensity Variation," National Library of Medicine, Mar. 6, 2001; 103(9):1206-11.

Keilers, C.H., Jr. et al., "Damage Detection and Diagnosis of Composites Using Built-In Piezoceramics," *SPIE* vol. 1917 *Smart Structures and Intelligent Systems* (1993):1009-1015.

Kimura, B.J. et al., "Value and Limitations of Intravascular Ultrasound Imaging in Characterizing Coronary Atherosclerotic Plaque," *Am. Heart J* Aug. 1995; 130(2):386-96.

Kristensen, S.D. et al., "Insights into the Pathophysiology of Unstable Coronary Artery Disease," *Am J. Cardiol* Sep. 4, 1997;80(5A):5E-9E.

Kullo, I.J. et al., "Vulnerable Plaque: Pathology and Clinical Implications," *Ann Intern Med* Dec. 15, 1998;129(12):1050-60.

Lin, M. et al., "Development of Smart Layer for Built-In Diagnostics for Composite Structures," Proceedings of 13th Annual Technical Conference on Composite Materials, Sep. 21-23, 1998, Baltimore, Maryland.

Lin, M. et al., "Built-In Structural Diagnostics for Composite Structures," Proceedings of SEM Spring Conference on Experimental and Applied Mechanics and Experimental/Numerical Mechanics in Electronic Packaging III, Jun. 1-32, 1998, Houston, Texas.

Lin, M. et al., "Composite Structures with Built-In Diagnostics," *Materials Today*, vol. 2(2), Jun. 1999, 18-22.

Lin, M. et al., "Manufacturing of Composite Structures with a Built-In Network of Piezoceramics," Dissertation submitted to Dept. of Mechanical Engineering, Stanford University, Dec. 1998.

National Institutes of Health, Prospective Grant of Exclusive License: Development of Instruments for Diagnostic and Surgical Applications Based on Spectroscopic and Hyperspectral Imaging Techniques, Federal Register, vol. 65, No. 64, Apr. 3, 2000, Notices.

Naghavi, M. et al., "New Developments in the Detection of Vulnerable Plaque," *Curr Atheroscler Rep* Mar. 2001;3(2):125-35.

Roh, Youn-Seo, "Built-In Diagnostics for Identifying an Anomaly in Plates Using Wave Scattering," Disseration submitted to Dept. of Aeronautics and Astronautics, Stanford University, Sep. 1998.

Tracy, M. J., "Identifying Impacts in Composite Plates with Piezoelectric Sensors," Dissertation submitted to Dept. of Aeronautics and Astronautics, Stanford University, May 1996.

Tracy, M. et al., "Identifying Impact Load in Composite Plates Based on Distributed Piezoelectric Sensor Measurements," *SPIE* vol. 2717 *Smart Structures and Integrated Systems* (1996):231-236.

VonBirgelen, C. et al., Plaque Distribution and Vascular Remodeling of Ruptured and Nonruptured Coronary Plaques in the Same Vessel: An Intravascular Ultrasound Study in vivo., *J Am Coll Cardiol* Jun. 1, 2001;37(7):1864-70.

Yang, S. et al., "Design and Fabrication of a Smart Layer Module in Composite Laminated Structures", *Smart Mater. Struct.* 14 (2005) 315-320.

* cited by examiner

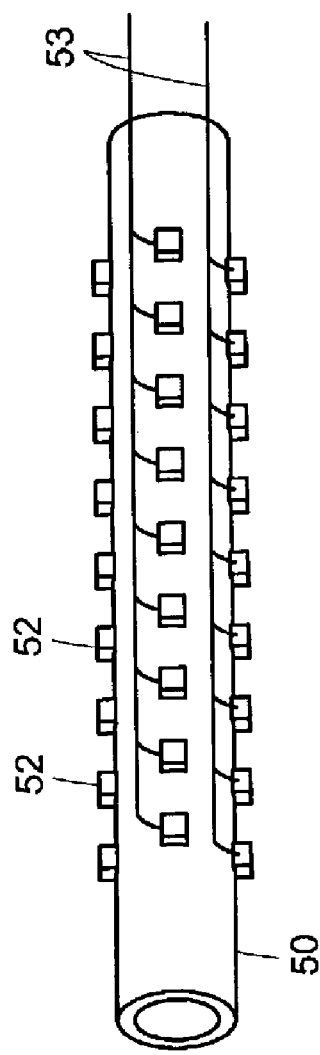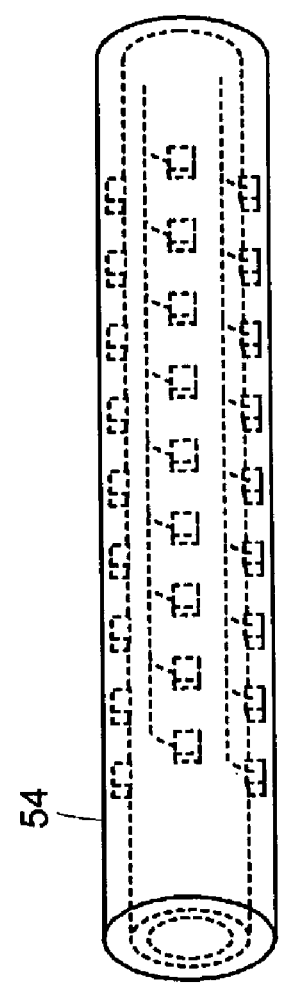

CATHETER LESION DIAGNOSTICS

CROSS-REFERENCE TO RELATED APPLICATION

This application claims priority from U.S. provisional patent application Ser. No. 60/329,193, filed on Oct. 12, 2001, which is incorporated herein by reference in it entirety.

FIELD OF THE INVENTION

This invention relates to catheter lesion diagnostics.

BACKGROUND

In an angioplasty procedure, a catheter carrying an inflatable balloon is threaded through a body lumen. The balloon is positioned at the location of a lesion which is occluding the lumen and inhibiting flow of body fluid. The balloon is inflated to apply a radial force about the lesion to force the lumen open. The balloon is then deflated and the catheter withdrawn from the body. A stent may be positioned at the location of the lesion, either simultaneously with the dilation or at a later time, to reduce the likelihood of reocclusion of the vessel.

SUMMARY

In one aspect, the invention features an expandable catheter including a catheter body having an expandable portion. The expandable portion has a plurality of spaced piezoelectric elements. A controller controllably produces and receives the signals from select elements of said plurality.

In another aspect, the invention features a balloon catheter. The balloon catheter includes a catheter body having an expandable polymeric balloon. The expandable balloon includes a first layer and a second layer, and the first layer has embedded therein a plurality of piezoelectric transducers.

In a further aspect, the invention features a method that includes providing a catheter having an expandable member thereon. The expandable member has a plurality of spaced piezoelectric elements. The method also includes locating the balloon in a vessel near a region of interest, and inflating the balloon. The invention further includes launching an acoustic signal into the region of interest using a first piezoelectric element, and detecting the acoustic signal using a second piezoelectric element.

In another aspect, the invention features a medical having a piezoelectric element which is located in a lumen to position the piezoelectric element near a region of interest. Using the piezoelectric element, an acoustic signal is launched and/or received from the region of interest using the piezoelectric element. An acoustic signal from the region of interest is detected.

In another aspect, the invention features a member for delivery into a lumen including a piezoelectric member, and a controller for launching and/or receiving an acoustic signal into and/or from the lumen using the piezoelectric element. The controller analyzes acoustic signal from the region of interest to indicate a mechanical or morphological property below the surface of the region.

In aspects, the invention includes one or more of the following. The expandable member can be an inflatable balloon. The balloon can be substantially non-distendable. The balloon can include a generally cylindrical expandable portion, and the expandable portion can include the piezoelectric elements. The piezoelectric elements can be in a regular array. The piezoelectric elements can be disk shaped members. The piezoelectric elements can be embedded in a polymer layer. The polymer layer can have a thickness of about 0.005 inch or less. The balloon can include a first layer of non-distendable polymer selected from, for example, PET and/or nylon. The piezoelectric elements can be embedded in a second layer of a different polymer than the first layer. The second polymer layer can be an outer layer. The second layer can be more compliant than the first layer. The controller can produce an acoustic signal from a first piezoelectric element and receives the signal in another piezoelectric element. The signal can be received by multiple other piezoelectric elements. The catheter can include a stent positioned over the expandable member.

The signal is analyzed to indicate a mechanical or morphological property of tissue of the region, particularly below the surface of the region. Mechanical properties include density, impedance, or viscoelastic properties. The signal may be indicative of soft lipid or brittle plaque. A radial map of the property and/or an axial map of the property is provided. The medical device is an elongate flexible device. The device is delivered into the vascular system. The device includes an inflatable balloon. The piezoelectric element is embedded in a polymer. The medical device includes a plurality of piezoelectric elements. The signal is detected after dilation of the region and/or during dilation of the region. A stent in the region includes a drug.

In additional aspects, the invention features embodiments including a wire and/or a catheter having piezoelectric elements controlled as described herein.

Further aspects involve combinations of embodiments.

The details of one or more embodiments of the invention are set forth in the accompanying drawings and the description below. Other features, objects, and advantages of the invention will be apparent from the description and drawings, and from the claims.

DESCRIPTION OF DRAWINGS

We first briefly describe the drawings.

FIGS. 1A and 1B are schematics of a diagnostic catheter in a body lumen, while

FIG. 2A is a schematic of an array of piezoelectric elements in proximity to a lesion feature, while FIGS. 3A-3D illustrate construction of a diagnostic catheter.

DETAILED DESCRIPTION

Figure 1A:
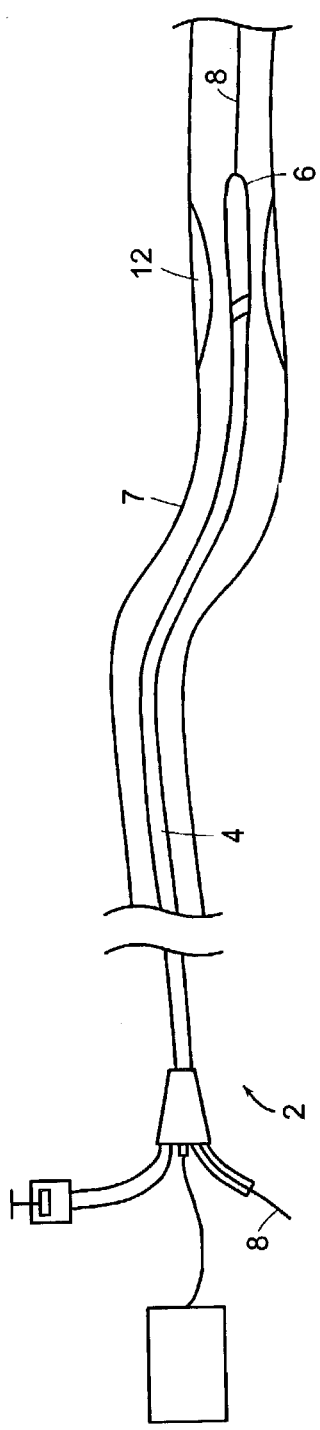
Figure 1B:
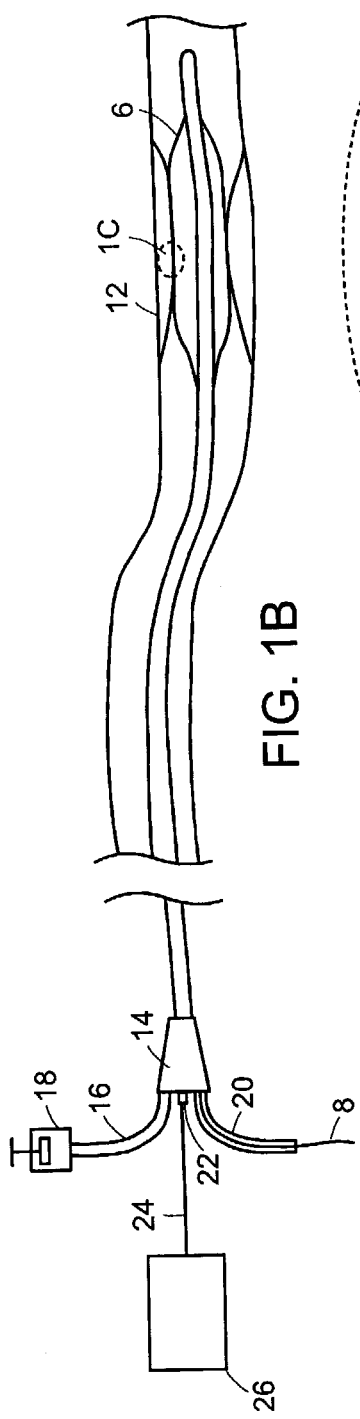
Figure 1C:
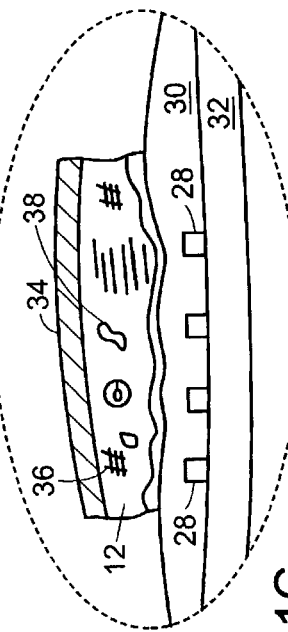
FIG. 1C is an expanded cross-sectional view of the region C, in FIG. 1B.

Referring to FIGS. 1A and 1B, a diagnostic catheter system 2 includes a catheter body 4 carrying near its distal end an expandable member 6, in this case an expandable balloon. The catheter can be delivered into a vessel 7 by sliding it over a guidewire 8 to locate the expandable member 6 near a lesion 12 which is partially occluding the vessel lumen. Referring particularly to FIG. 2B, the expandable member is expanded to position the outer surface of the expandable member in close proximity, e.g., into contact with, the outer surface of the lesion. As illustrated, the proximal end of the catheter includes fitting 14 with a port 16 that accesses an internal catheter lumen which directs inflation fluid between an inflator 18 to the interior of the expandable member. A port 20 communicates with an internal catheter lumen opening at the catheter distal end to facilitate delivery over the guidewire 8. A port 22 includes a communication conduit 24 which is connected between a controller 26 and piezoelectric diagnostic apparatus associated with the expandable member.

Referring particularly to FIG. 11C, the diagnostic apparatus includes an array of piezoelectric elements 28 carried by the expandable member 6. The elements 28 are spaced at regular intervals and, in this embodiment, are embedded within an outer layer 30 of the wall structure of the balloon, which also includes an inner layer 32. The inner layer 32 may be, for example, a relatively noncompliant material, such as polyethylene terephthelate, so that the relative position of the elements 28 in the array region remain substantially constant as a function of inflation pressure. The outer layer 30 may be a more compliant material, such as Hytrel, selected to generally conform to the outer surface of the lesion and/or have a desired acoustic impedance. The piezoelectric elements are operated to diagnose the nature of the lesion 12.

As illustrated, the lesion 12 is a deposit on the vessel wall 34. The lesion is generally not homogenous. For example, it may include heavily calcified, brittle regions 36 intermixed as a function of depth and axial positions with more compliant lipid pools 38. The presence, amount, and location of such regions can affect the angioplasty procedure. The success of the angioplasty procedure and the likelihood of reocclusion can be dependent upon the nature of the lesion. For example, in blood vessels, the lesion is typically in the form of plaque, which can be made of disparate components such as hard, calcified deposits and/or softer lipid deposits. Some lesions are not safely dilated because they may rupture and release particles into the blood stream. For example, a concentration of brittle calcified material can crack and break off upon compression.

Figure 2A:
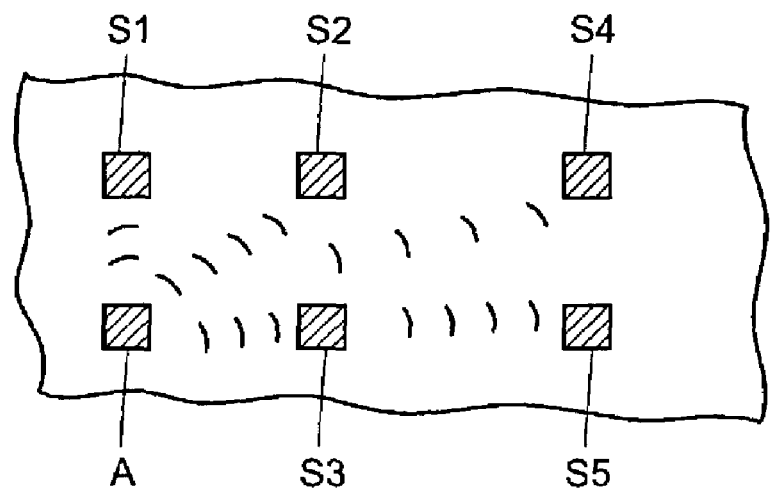
Figure 2B:
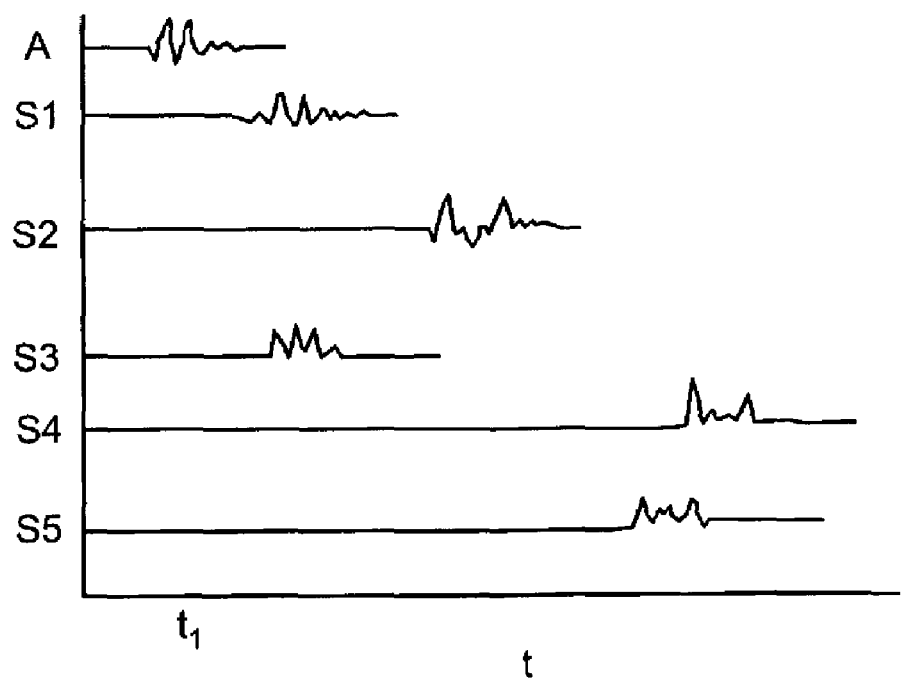
FIG. 2B is a graph illustrating acoustic signal generation and sensing from FIG. 2A.

Referring as well to FIG. 2A, the piezoelectric elements work in coordination to diagnose such features. A portion of the array, elements A and S1-S5, is illustrated about a region 40, which may be, for example, a lipid pool located within a more brittle plaque matrix. The element A is operated to launch an acoustic signal into the plaque, while elements S1-S5 are operated to receive the signal. Referring as well to FIG. 2B, the signal A, having a desired signal shape is launched at a time $t_1$. The elements S1-S5 detect this signal after it propagates through the lesion. The timing and shape of the signal varies as a function of the location of each element and acoustic impedance of the structures encountered by the acoustic pulse due to reflection and refraction of the signal. As a result, by analyzing the wave shape and timing of multiple pulses from multiple elements, an axial and radial spatial map of the acoustic features and hence the composition of the lesion can be determined. The map can, for example, be compared with standard lesion brittleness patterns to determine the desired conditions for angioplasty, whether a stent should be inserted, or whether angioplasty is not suitable.

Acoustic diagnostics can be used to interrogate the mechanical material properties. The diagnostics can be passive or active. Active diagnostics involve launching a controlled signal into the material and determining the mechanical properties from reflections and from refractions of the signal deep within the material as the wave encounters structures having different acoustic impedances. Passive diagnostics involves detecting acoustic waves as the material responds to normal stress. One system utilized for diagnostics of composite construction materials is the Stanford Multi-Actuator Receiver Transduction (SMART) layer.

The SMART layer is a dielectric film carrying a distributed network of piezoelectric elements that serve as both sensors and actuators. The layer is integrated with a composite structure. In active mode, some of the disks are operated in an actuator mode to launch acoustic wave signals into the material, while other disks are utilized as sensors to detect the signals. In the passive mode, multiple disks act as sensors to detect stress response. The piezoelectric elements 28 are preferably small ceramic units, e.g., of PZT. A suitable unit is used in the SMART layer system, which has an array of disk shaped PZT elements having a diameter of desired size (e.g., about 0.25 inch, less than about 0.25 inch, less than about 0.125 inch). The disks may be embedded in a polymer film having a thickness of about 0.002 inches. Such films may be bonded directly to the interior or exterior of a medical balloon. Alternatively, the array is incorporated into the balloon during balloon manufacture.

The construction and control of a piezoelectric array for diagnosing and monitoring material properties is further discussed in M. Lin and F-K. Chang, Materials Today, Vol. 2, Issue 2, Jun. 1999 ("Lin and Chang I"), the entire contents of which are incorporated herein by reference. For example, Lin and Chang I state the following:

"Recent advances in sensing technologies, material/structural damage characterization, and computation and communication have resulted in a significant interest in developing new structural diagnostic technologies. Intended for monitoring the integrity of both new and existing structures, a structural diagnostic system would be able to detect damage in real time with minimum human involvement. To use distributed sensors to monitor the 'health' condition of in-service structures, the sensor signals would have to be interpreted accurately through real-time data processing to reflect the in-situ condition of the structures. The entire system could be integrated to perform automated real time inspection and damage detection.

Built-In Structural Health Monitoring

Typically, such a built-in diagnostic system, in addition to the host structures, would consist of at least two major components: a built-in network of sensors for collecting sensor measurements and software for interpreting the sensor measurements in terms of the physical conditions of the structures . . . . Depending on the inputs, structural diagnostic techniques can be divided into two types: passive sensing systems (i.e., with sensors only and without known inputs) and active sensing systems (i.e., with actuators as well as sensors and with known inputs).

Passive Sensing Diagnostics

For a passive sensing system, only sensors are installed in the structures. Sensor measurements are constantly taken in real time and compared with a set of (healthy) reference data while the structures are in service. The passive system estimates the condition of the structures based on the data comparison. Hence, the technique of data comparison for interpretation of structural conditions is crucial for a reliable system. The system would require either a data bank with a history of pre-stored data or a structural simulator that can generate the needed reference data.

Because the input energy to the structures is typically random and unknown, the sensor measurements reflect the corresponding structural response to the unknown inputs. This type of diagnostics has been applied primarily to determine the unknown inputs (external loads, temperature, pressure, etc.) that cause the change in sensor measurements.

Active Sensing Diagnostics

For an active sensing system, known external mechanical or non-mechanical excitations are input to the structures through built-in devices such as transducers or actuators. Since the inputs are known, the difference in the local sensor measurements based on the same input is strongly related to a physical change in the structural condition such as the introduction of damage. By using an appropriate algorithm to interpret the difference in sensor measurements, structural damages can be clearly identified.

The SMART Layer Approach

Recently, a method to implement a network of distributed piezoelectric sensors/actuators has been developed at Stanford University . . . . This method is based on the flexible circuit printing technique which is commonly used in the electronics industry. The fabricated thin, flexible sheet supporting a network of actuators/sensors is referred to as a SMART (Stanford Multi-Actuator-Receiver Transduction) Layer . . . .

The SMART layer is made of a dielectric film with a distributed network of piezoelectric disks serving as both sensors and actuators . . . . Numerous potential materials in the market were screened and Kapton® film was selected to make the layer. The thickness of the film is about 0.002 inch.

Piezoelectric ceramic (PZT) was selected to form the sensor network, and the size of the piezo-disks can be chosen at the discretion of the users. For the current design, a 0.25" diameter 0.01" thick disk was used. The pattern of the piezoceramic network and the distance between the piezoelectric disks can be designed to suit the specific application.

The major processing steps of manufacturing the SMART layer involve printing and etching a conductor pattern onto a dielectric substrate, laminating a dielectric cover layer for electrical insulation, and mounting the array of piezoceramics on the circuit. For laminated composites, the SMART layer can be considered as an extra ply laid down between composite plies or patched on the surfaces of the laminates during lay-up. After co-curing in an autoclave, the resulting composite laminates would have an integrated network of active piezoelectric transducers that can be used to send and receive diagnostic signals within the composite structures.

Applications

Once the SMART layer is integrated with the structure, it can retrieve information that relates to the environmental or physical changes in the structural condition. The SMART layer can function as a passive or an active diagnostic system, depending on the usage of the piezo-disks. To use as a passive diagnostic system, the piezo-disks are used as sensors to measure the strain values of the structure. To use as an active diagnostic system, one piezo-disk is used as an actuator to input a diagnostic signal while another piezo-disk is used to retrieve the diagnostic signal. The role of each piezo-disk can be reversed to work either as an actuator or a sensor, forming multiple combinations of actuator-sensor pairs. In both cases, the information retrieved from the structure can be used to infer the health of the structure." (Lin and Chang I, pages 18-20.)

The construction and control of a piezoelectric array for diagnosing and monitoring material properties also is discussed in F-K. Chang, "Manufacturing and Design of Built-In Diagnostics for Composite Structures," Progress Report to the U.S. Army Research Office P00001, 1997, the entire contents of which are incorporated herein by reference.

Additionally, the construction and control of a piezoelectric array for diagnosing and monitoring material properties is discussed in M. Lin and F-K. Chang, "Development of SMART Layer for Built-in Diagnostics for Composite Structures," The $13^{th}$ Annual ASC Technical, 1998 ("Lin and Chang II"), the entire contents of which are incorporated herein by reference. For example, Lin and Chang II state the following:

Abstract

An investigation was performed to develop an efficient and economical technique for manufacturing composite structures with built-in diagnostics. A smart layer containing an embedded network of distributed piezoelectric ceramics (PZT) was developed using the printed circuit technique. Mechanical tests were conducted to assess the integrity of composites embedded with the smart layer. The results showed that no significant degradation appeared in the composites due to the presence of the smart layer. The fabricated smart layer was used to demonstrate several structural diagnostic applications, including: monitoring the cure progress, identifying impact, and detecting damage of composites.

Approach and Results

A smart layer which contains an embedded network of distributed piezoelectric ceramics (PZT) has been developed. The smart layer is analogous to one extra ply that can be laid down between composite plies or on the surface of the laminates during composite layup. After co-curing in an autoclave, the resulting composite laminate would have an integrated network of piezoceramics that can be used to send and receive diagnostic signals for monitoring the structure.

A reliable and simple manufacturing technique was proposed to fabricate the smart layer . . . . The process is based on the flexible printed circuit idea that is used in the electronics industry, with modifications to accommodate the composite manufacturing process. The major processing steps involve printing and etching a conductor pattern onto a dielectric substrate, laminating a dielectric cover layer for electrical insulation, and mounting the arrays of piezoceramics on the circuit. Several smart layers have been fabricated and embedded inside Gr/Ep composite laminates successfully." (Lin and Chang II, pages 1-2.)

The construction and control of a piezoelectric array for diagnosing and monitoring material properties also is discussed in M. Tracy, "Impact, Load Identification for Composite Plates Using Distributed Piezoelectric Sensors," Ph.D. dissertation, Department of Aeronautics, Stanford University, 1996, and M. Tracy and F-K. Chang, "Identifying Impact Load in Composite Plates Based on Distributed Piezo-sensors," The Proceeding of SPIE Smart, CA 1996, the entire contents of both of which are incorporated herein by reference.

The construction and control of a piezoelectric array for diagnosing and monitoring material properties additionally is discussed in YS. Roh, "Built-In Diagnostics for Identifying an Anomaly in Plates using Wave Scattering,"Ph.D. Dissertation, Department of Aeronautics, Stanford University ("Roh"), the entire contents of which are incorporated herein by reference. For example, Roh states the following:

"The basic principle of the structural health monitoring techniques is to use the change in the measurements by built-in sensors at the same location at two different times to determine the condition of the structures. Hence, the historical data of the response of the structures is crucial for the use of the technique. The accuracy of the identification depends strongly upon the sensitivity of sensors and the interpretation algorithm.

Typically, such a built-in diagnostic system, in addition to the host structures, would consist of at least two major components: a built-in network of sensors for collecting sensor measurements and software for the interpretation of sensor measurements in terms of the physical conditions of the structures. However, depending upon the inputs, the structural health monitoring systems can be divided into two types: passive sensing diagnostics without known inputs (with sensors only) and active sensing diagnostics with known inputs (with both sensors and actuators).

1.1 Passive Sensing Diagnostics

For a passive sensing system, only sensors are installed in the structures. Sensor measurements are constantly taken in real time, while the structures are in service, and are compared with a set of reference (healthy) data. The sensor-based system estimates the condition of the structures based on the data comparison. Hence, the technique of data comparison for interpretation of structural conditions is crucial for a reliable system. The system would require either a database that stores the history of pre-stored data or a structural simulator which could generate needed reference data.

Because the input energy to the structures is typically random and unknown, the corresponding sensor measurements reflect the response of the structures to the unknown inputs. This type of diagnostics has been primarily applied to the determination of the unknown inputs which cause the changes in sensor measurements, such as external loads, temperature, pressure, etc.

Examples of a passive sensing system are systems based on fiber optics, acoustic emissions, and piezoelectric sensors . . . .

1.2 Active Sensing Diagnostics

For an active sensing system, known external mechanical or non-mechanical loads are input to the structures through built-in devices such as transducers or actuators. Since the inputs are known, the difference in the local sensor measurements based on the same input is strongly related to a physical change in the structural condition such as the introduction of damage. Examples of the excitation inputs include wide-band signals such as impulse, or frequency sweeps that excite the structure over a wide frequency range. Frequency range of the input usually covers the lowest vibration modes . . . .

8.2 Specimen Preparation

Experiments are done on two aluminum plates of a thickness of 0.036 inch. To reduce the boundary effect, four piezos are attached around the center of the plate, forming a square of 6-inch sides. But later experiments showed that if the boundaries are at the distance of approximately the sensor-actuator spacing, the effect of the boundary on scatter signals is negligible.

The piezoceramic elements used are from the Piezo Kinetics. Inc. The selected material is PKI400, which is of the Lead Zirconate Titanate (PZT) type. A thin disc shape is used with a 0.25-inch diameter and a 0.010-inch thickness. Both circular surfaces are plated with silver to form electrodes. Polarization is along the symmetry axis of the cylinder. Two pieces are attached on the top and bottom surfaces of the plate, and are electrically connected to generate flexural or antisymmetric waves, instead of in-plane or symmetric waves.

The piezo discs are bonded to the plate with conductive epoxy, and the whole aluminum plate can be used as the ground terminal. Nonuniformity of the bonding for different piezo attachments creates slight differences in transfer function for different measurement paths. But the final identification results are not affected by this nonuniformity because the identification routine makes use of RSS, which effectively eliminates the sensor/actuator effect. (Roh, pages 2-3, 4, and 74-76.)

The construction and control of a piezoelectric array for diagnosing and monitoring material properties is further discussed in M. Lin, "Manufacturing of Composite Structures with a Built-In Network of Pizeoceramics," Ph.D. Dissertation, Department of Mechanical Engineering, Stanford University ("Lin"), the entire contents of which are incorporated herein by reference. For example, Lin states the following: . . . . A passive sensing system contains only sensors so it takes unknown external inputs to excite the structure and then monitors the structural response. Examples of a passive sensing system include structures with distributed strain gauges . . . fiber optic sensors . . . , and accelerometers . . . . An active sensing system contains actuators as well as sensors so it can generate known (controlled) inputs internally to excite the structure and then monitor its response. An example of an active sensing system is a structure integrated with distributed piezoceramics . . . .

The intent is to adapt the flexible printed circuit concept into the manufacturing of integrated structures. The proposed concept uses this technique to make a large, thin flexible sheet that contains a network of distributed piezoceramics connected by printed circuits all—properly insulated . . . . This sheet with the piezoceramic-network can be used like an extra ply that's either embedded inside or bonded on the surface of composite laminates. It would give the composite the added functionality of exciting the structure (actuating) and collecting information about the structure (sensing), besides just carrying load. This sensor layer will be referred to as the Stanford Multi-Actuator-Receiver Transduction Layer, or SMART Layer for short . . . .

The SMART Layer utilizes a layered construction: It starts out with a layer of printed circuit on a dielectric substrate. Next, a dielectric coverlayer is bonded on top to completely insulate the circuit, except for the locations where the piezoceramics are to be mounted. At these access points, a hole the size of the piezoceramic is punched-out in the coverlayer. The piezoceramics are then mounted through these holes, in contact with the underlying circuit. Lastly a ring of dielectric material is deposited around the circumference of each piezoceramic. This ring serves three functions: 1) to insulate the side of the piezoceramic so carbon fibers don't come in contact with its bottom electrode, 2) to seal the gap between the piezoceramic and the access hole in the cover layer so carbon fibers don't come in contact with the printed circuit within, 3) to help secure the piezoceramic onto the substrate.

There are some unique features of this new design that should be pointed out: Before embedding inside composite, the piezoceramics are 'un-encapsulated' i.e., the piezoceramics are not encased in another material such as an electronic potting compound. Rather, the piezoceramics are entirely exposed except for the bottom side that's bonded to and insulated by the dielectric substrate . . . . This minimal insulation approach has some advantages: First, the composite surface can be used as electrical ground since the top side of all piezoceramics are electrically connected together by carbon-fibers, turning their conductivity into an advantage—this effectively reduces the number of wires in the network by half. Also, by exposing the piezoceramics to the composite, the matrix resin of the composite itself is able to flow around the piezoceramic and encapsulate it —this forms an intimate contact between the structure and the actuator/sensor without a secondary medium in between, thus allowing optimum mechanical coupling. Another feature is that the pre-punched holes in the cover layer can be used as a template to position the piezoceramics—this allows the piezoceramics to be placed very Quickly with good accuracy, thus speeding-up the manufacturing process.

4.3 Material Selection

For the SMART Layer design presented in the last section, the materials chosen for each of the components are summarized in Table 4.1.

TABLE 4.1

Materials selected for the components in the SMART Layer.

| Component | Function | Material Choice |
|---|---|---|
| sensor/actuator | generate/receive signal | PZT (lead-zirconate-titanate) |
| dielectric substrate | electrical insulation, component support | Kapton ® |
| adhesive | bonding | acrylic adhesive |
| wire | carry signal | copper |
| dielectric ring | electrical insulation | epoxy |

5.1 SMART Layer Manufacturing Procedure

The manufacturing of the SMART Layer is a multi-step process. It involves printing a circuit on a dielectric substrate, laminating-on a cover layer and the PZTs, and coating with an epoxy insulation ring . . . .

1. Surface Preparation
   a. Preclean laminate
      . . . This is most often done with a chemical process: a dip or spray of hydrochloric acid (HCl) to remove the chromate treatment followed by a water rinse and dry.
   b. Microetch
      A microetch with sodium persuiphate (NaSO₄) will promote resist adhesion in subseQuent imaging operations. This is again followed by a water rinse and dry.
2. Print-and-Etch Circuit
   a. Print Resist Pattern
      There are two popular methods of pattering the resist in the industry today: screen printing and photo-imaging . . . . Photoimaging is a multistep process: First a sheet of dry resist film is laminated on the copper surface using a hot roll laminator (230° F., 40 psi). The resist is then exposed to UV light through a phototool. The phototool is simply a transparent film with an image of the circuit on it. The phototool is placed in intimate contact with the copper-clad laminate using a vacuum frame. The laminate is then exposed to UV light for a short time (3-20 sec. depending on resist type and lamp intensity). For a positive-acting resist, area not shielded from the UV light by the circuit image dissociates, and can be washed away in a developer solution, leaving just the circuit-pattern resist behind . . . . A common developer is 1% sodium carbonate in water at 90° F. A rinse and dry step follows.
   b. Etch Copper
      Next the "patterned" copper is ready to be etched to obtain the electrical circuit. The way this works is as follow: Bare copper surface that comes in contact with the etchant will be dissolved away while surface covered by the (etch) resist will be protected from the etchant and remain as a circuit conductor pattern . . . . Several etchants are available for copper, such as ferric chloride, cupric chloride, and hydrogen peroxide/sulfuric acid . . . . The etch process is typically done on a conveyorized spray-etch line . . . . After the circuit pattern is etched out, the laminate is rinsed with water to stop the etching.
   c. Strip Resist
      The etch resist is only used for intermediate processing and must be removed before subseQuent steps. For most resists, the stripping process is simply a spray-wash under a more powerful form of the developer solution, such as 2% sodium hydroxide at elevated temperature (130° F.). This is followed by a rinse and dry.
3. Laminate coverlayer
   a. Punch access holes
      There are many ways to punch out the access holes on the coverlayer, ranging from manual punching, die stamping, to numerical-control (NC) drilling . . . .
   b. Laminate coverlayer
      After the coverlayer is punched, it is laid on top of the circuit substrate. The coverlayer is placed such that the holes are aligned with the circuit contact locations underneath. The assembly is placed in the vacuum lamination machine with a layer of Teflon-coated peel ply on the top and bottom. Heat and pressure are applied and held for 15 minutes after it has reached lamination temperature (360-390° F.). The vacuum is maintained during cooling until the part has returned to room temperature.
4. Laminate PZT
   To create a reliable electrical connection between the PZT and the etched circuit, they should be soldered together . . . . The PZTs and the wires can be soldered together in an automatic fashion: First, solder is applied to the PZT and the wire contacts separately. Then, the two components are placed together and applied heat to reflow the solder. Upon cooling, the two components are consolidated together. To apply solder onto the components' surface, there is also an automatic method than can be used-electroplating.
   a. Tin/lead plating of wire contact with PZT
      . . . By using the component (PZT or copper wire) as the cathode and a bar of tin/lead alloy as the anode and applying an electropotential between them, the tin and lead ions will migrate from the anode through the electrolyte and deposit on the cathode's surface. The composition of the alloy deposited is controlled through the applied current density . . . .

b. Bonding PZT

The layup sequence for the PZT lamination step is depicted in FIG. 5.6 [not shown]. First, three layers of bleeder material is laid down on the surface of the vacuum lamination machine for cushion. On top, one layer of Teflon coated peel ply is added. Next, the printed circuit laminate is laid down with the contact holes facing upward. Then the PZTs are placed on the printed circuit substrate using the access holes in the coverlayer as a guide. Again, another layer of Teflon coated peel ply is placed on top. Finally, another three layers of bleeder are added for cushion.

The vacuum lamination machine is then turned on to apply heat and pressure for bonding. The temperature is held for 30 minutes after it has reached 390° F. At that temperature both the solder and the acrylic adhesive would melt to electrically connect and mechanical bond the PZTs to the printed wires. During cooling, vacuum is continually applied until the assembly has returned to room temperature.

5. Deposit Epoxy Ring a. Deposit epoxy ring

The goal is to deposit a ring of epoxy around the perimeter of the PZT, similar to filling a fillet. This can be done efficiently with an automatic epoxy dispensing system, such as Liquid Control Corporation/Dispensit's 400-S automatic epoxy dispensing system . . . .

b. Cure epoxy ring

The assembly is placed in an oven and cured at 200° F. for one hour. After curing the epoxy should form a hard ring around the PZT that insulates its side and holds it firmly onto the substrate film.

After the addition of the epoxy rings, the SMART Layer is considered finished. It is now ready to be embedded into a composite laminate . . . .

The procedure for laying up a composite panel with a SMART Layer embedded inside is the same as the conventional composite layup procedure. The SMART Layer is simply treated as an additional ply inserted during layup. After the plies are stacked together, it is best to place the laminate back in the vacuum lamination machine and apply vacuum for compaction—this would firmly press all the plies together using a uniform pressure.

The bagging procedure for the embedded laminate is also similar to that for a regular laminate; the only exceptions are: 1) The bleeder layers should be placed on both top and bottom of the composite laminate, proportional to the number of composite plies above and below the SMART Layer. 2) The leads from the SMART Layer should be covered with a piece of Teflon film to protect them from resin overflow and sticking to the peel ply. A caul plate (of approximately 0.06"thickness) should always be used on top of the perforated nylon film to keep the surface of the laminate flat . . . during cure.

The cure cycle for the embedded panel is the same as for a regular panel—typically just following the manufacturer recommended cure cycle. When the cure is finished, the composite panel with the embedded SMART Layer is ready to be used . . . (Lin, pages 1-2, 14, 15, 16, 22, 23-24, 25, 26, 27, 28, 29, 30-31, 32-33 and 34.

The piezoelectric members typically induce a signal in the ultrasonic range, e.g. in the 100-300 kHz range. Operation and data analysis is further described, for example, in "Damage Detection and Diagnosis of Composites Using Built-In Piezoceramics," C.H. Keilers and F.-K. Chang, Proceedings S.P.I.E. The International Society for Optical Engineering, Issue 1917, pp. 1009-1019 (1993) ("Keilers and Chang"), the entire contents of which are hereby incorporated by reference. The abstract of Keilers and Chang is reproduced below:

An investigation was performed to develop a technique for using built-in piezoelectrics to detect delaminations and to estimate their size and location in laminated composite structures. Both experimental and analytical work were conducted in the study. Piezoceramics were utilized as sensors for receiving signals and as actuators for dispatching diagnostic waves. A diagnostic technique was developed which combines an electromechanical structural model with an iterative damage identification algorithm to form a closed loop. The structural model was used to predict the frequency response of normal and delaminated structures excited by actuators. The identification algorithm compares the calculation with the data to find a best estimate of delamination size and location. The technique first compares the measured dynamic response to a baseline. If they disagree, the technique searchres through the possible locations and sizes of delaminations using the structural model and compares the results with the measurements. The loop terminates when the calculated and the measured frequency responses agree. Tests on composite beams with implanted delaminations were conducted to verify the model and predictions. Overall, the predictions agreed with the data. (Keilers and Chang, Abstract.)

Referring to FIGS. 3A-3D, a balloon may be formed by extruding a tube 50 of a desired balloon polymer or polymers. The tube is then patterned with an array of piezoelectric elements 52. The pattern is located on the portion of the tube that will become the expandable portion of the balloon. The elements may be fixed to the tube using an adhesive, friction fit, or surface melting. A series of communication conduits 53, e.g., metal or conductive polymer wires are connected to the elements.

Referring particularly to FIG. 3B, the tube 50 carrying the array is next coated with an outer polymer layer 54. The coating may be done by dipping. Alternatively, the outer layer 54 is provided by extruding the polymer over the tube 50. The extrusion is carried out using a die having an annular opening through which the polymer is extruded and a central opening within the annulus, through which the tube 50 is drawn. The ends of the communication conduits 53 extend beyond the tube.

Figure 3C:
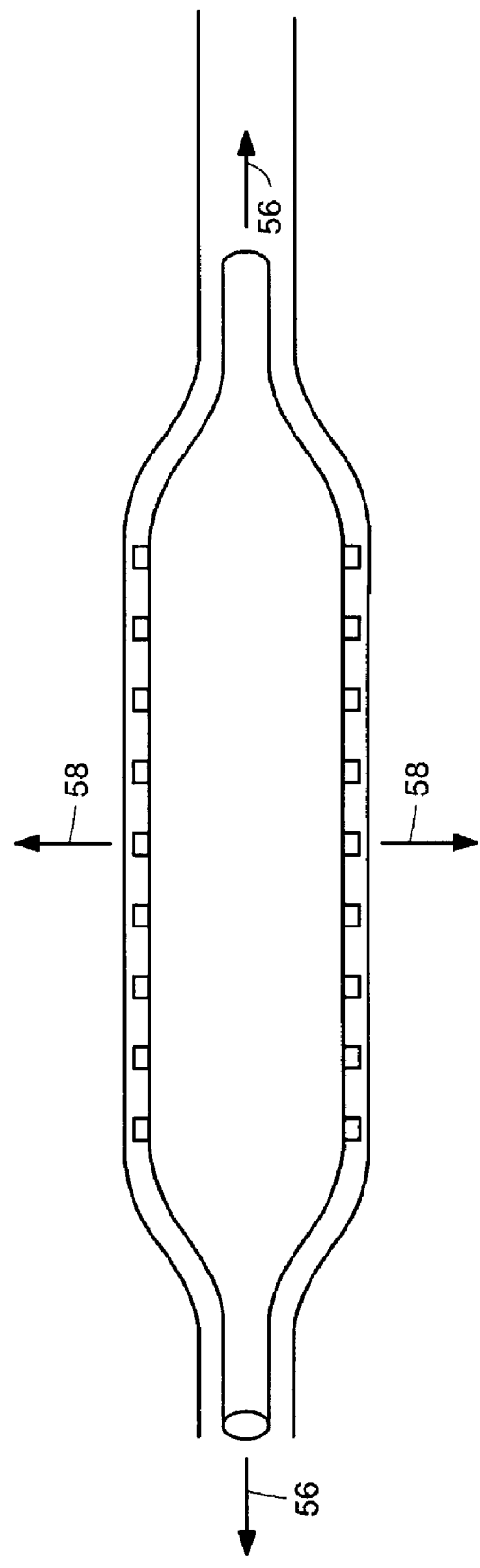

Referring particularly to FIG. 3C, the multilayer tube is blown into a balloon by free blowing or mold forming. In the case of a balloon including biaxially oriented layers, the tube is heated while the ends of the tube are drawn axially (arrows 56) and the interior is pressurized to radial expand (arrows 58) the central portion of the tube including the element array. Multilayer coextrusion of medical balloons is described in U.S. Ser. No. 09/798,749, filed Mar. 2, 2001, and published on Nov. 7, 2002 as U.S. Patent Application Publication No. US 2002/0165523 A1, the entire contents of which are incorporated herein by reference. Balloon-forming is discussed in U.S. Ser. No. 09/950,195, filed Sep. 10, 2001, now abandoned, the entire contents of which are incorporated herein by reference. The contents of U.S. Ser.

No 09/950,195 are provided in Bertolino et al., U.S. Pat. No. 6,946,092, which is a continuation application of U.S. Ser. No. 09/950,195.

Figure 3D:
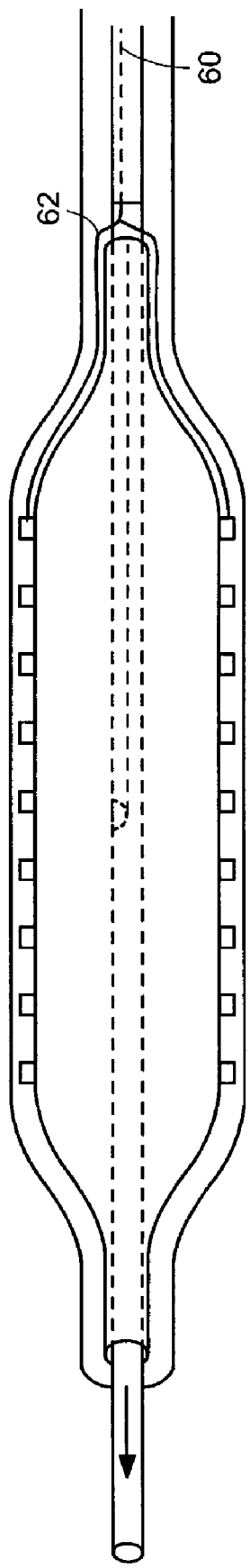

Referring as well to FIG. 3D, the balloon is attached to the catheter body by bonding balloon sleeves using, e.g., an adhesive or melt bonding. The communication conduit is directed through the catheter sidewall into a lumen 60. The lumen opening is covered by epoxy 62.

As discussed above, the balloon may be a noncompliant balloon including a layer of non-distendable polymer, such as PET or the like. Alternatively, the balloon may be a compliant balloon that stretches upon expansion. In this case, the balloon can closely conform to larger irregular lesion or vessel features to position a large number of the elements close to the feature. The balloon is preferably a multilayer balloon. The multilayer balloon may include more than the two layers above. For example, the balloon may include an outer layer in which the piezoelectric elements are embedded, a middle layer that provides high tensile strength and low distentibility an inner layer that provides a desired acoustic function, such as absorption or reflection of acoustic energy emitted by the element that is directed back toward the catheter. The middle and the inner layer may be formed by coextruding the initial tube. In embodiments, multiple layers may be provided over the piezoelectric elements to, e.g., provide desirable acoustic properties. For example, a hydrophilic layer (e.g., a hydrogel) may be provided to enhance transmission through blood or water. The balloon and catheter can be sized for the target vessel. For example, for blood vessels, the balloon has a length of about 3 to 10 cm and an inflated diameter of about 3 to 15 mm.

The analysis of the acoustic signals can be carried out in various ways to interrogate the mechanical properties. For example, the refraction and reflection of signals can yield a density or acoustic impedance map of the lesion structures. Alternatively, an average density, compliance measure, or acoustic impedance can be determined and compared to standard values based on historical angioplasty data. The devices to may be operated as multiple transducers that can be used to measure certain properties (e.g., viscoelastic properties) of a lesion in a body lumen. The balloon is typically expanded to place the elements in close proximity to or in contact with the lesion. But the balloon can be expanded to pressurize the lesions and diagnosis may be carried out as a function of pressure. Dilation of the vessel can be carried out by the diagnostic balloon catheter by inflating to dilation pressures. Diagnosis can be conducted before and after dilation. In addition, pressure can be monitored across the array during dilation by operating the elements in a passive mode. In addition, a stent or stent graft can be positioned over the balloon and placed by the catheter. The transducer can be operated in a receiving mode to monitor the force on the ends of the stent compared to the center or the stent. The system can be useful in drug delivery. For example, the insertion of drugs into the lesion can be monitored by monitoring acoustic impedance changes in the lesion. Drug delivery can be accomplished with a drug coated balloon or a drug coated stent. Drug delivery is described in Saharan et al., U.S. Pat. No. 5,954,706, the entire contents of which is incorporated herein by reference. In addition, the piezoelectric elements can be arranged in an asymmetric pattern.

While certain embodiments of balloons are described above, the piezoelectric elements can be applied to other medical devices that can be used in body lumens (e.g., blood vessels) to evaluate the lumens (e.g., by measuring one or more characteristics of an aspect of the lumen, such as the viscoelastic properties of a lesion). As an example, piezoelectric elements can be used in conjunction with (e.g., by integrally forming with) a wire. In certain embodiments, such a wire can be used with a relatively narrow vessel, such as one in which the wire can be adjacent to (e.g., in direct contact with) a lumen lesion.

As another example, piezoelectric elements can be used in conjunction with (e.g., by integrally forming with) a non-expendable catheter. In certain embodiments, such a catheter can be used with a relatively narrow vessel, such as one in which the catheter can be adjacent to (e.g., in direct contact with) a lumen lesion.

Moreover, the devices disclosed can be used, for example, in diagnostics for various types of lesions. An exemplary and nonlimiting list of such lesions includes clots, hard plaque, soft plaque, refractory plaque and/or solid plaque. The lesions can be located in any body lumen of interest, including, for example, neuro lumens, carotid lumens and/or coronary lumens.

In addition, in some embodiments, the medical devices and systems can be designed so that the information of interest can be accessed remotely. For example, the system can be configured so that the signal sent to the controller is wireless.

Further embodiments are within the scope of the claims.

What is claimed is:

1. An expandable catheter, comprising
a catheter body having an expandable member, the expandable member including a plurality of spaced piezoelectric elements embedded in a first layer comprising a polymer and including a second layer comprising a non-distendable polymer, and
a controller that controllably produces and receives a signal from elements of said plurality.

2. The system of claim 1 wherein the expandable member is an inflatable balloon.

3. The system of claim 2 wherein the balloon is substantially nondistendable.

4. The system of claim 3 wherein the balloon includes a generally cylindrical expandable portion and the expandable portion includes said piezoelectric elements.

5. The system of claim 4 wherein the piezoelectric elements are in a regular array.

6. The system of claim 5 wherein the piezoelectric elements are disk shaped members.

7. The system of claim 1 wherein the first layer has a thickness of about 0.005 inch or less.

8. The system of claim 1 wherein the first layer comprises a different polymer from the second layer.

9. The system of claim 8 wherein the first layer is an outer layer.

10. The system of claim 9 wherein the first layer is more compliant than the second layer.

11. The system of claim 1 wherein the controller produces an acoustic signal from a first piezoelectric element and receives the signal in another piezoelectric element.

12. The system of claim 11 wherein the signal is received by multiple other piezoelectric elements.

13. The system of claim 1 including a stent positioned over said expandable member.

14. A balloon catheter, comprising
a catheter body having an expandable polymeric balloon, the expandable balloon including a first layer and a second layer, the first layer including embedded therein a plurality of piezoelectric transducers, the second layer comprising a non-distendable polymer.

15. A method, comprising
 providing a medical device comprising an inflatable balloon including a first layer comprising a polymer, and a plurality of spaced piezoelectric elements embedded in the first layer, and a second layer comprising a non-distendable polymer,
 locating the medical device in a lumen to position the piezoelectric element near a region of interest,
 launching and/or receiving an acoustic signal into and/or from the region of interest using the piezoelectric element,
 detecting an acoustic signal from the region of interest, and
 determining a mechanical property of the region of interest.

16. The method of claim 15 comprising analyzing the signal to indicate a mechanical or morphological property of tissue below the surface of the region.

17. The method of claim 16 comprising providing a radial map of said property.

18. The method of claims 16 or 17 comprising providing an axial map of said property.

19. The method of claim 15 wherein providing a medical device having a piezoelectric element comprises providing an elongate flexible device.

20. The method of claim 19 comprising delivering the device into the vascular system.

21. The method of claim 15 wherein providing a medical device having a piezoelectric element comprises providing a medical device having a plurality of piezoelectric elements.

22. The method of claim 15 comprising detecting said signal after dilation of the region.

23. The method of claim 15 comprising detecting said signal during dilation of said region.

24. The method of claim 15 comprising providing a stent in said region.

25. The method of claim 23 wherein the stent includes a drug.

26. A medical device, comprising
 a member for delivery into a lumen including an inflatable member comprising a first layer comprising a polymer, a plurality of spaced piezoelectric elements embedded in the polymer, and a second layer comprising a non-distendable polymer, and
 a controller for launching and/or receiving an acoustic signal into and/or from the lumen using the piezoelectric element, the controller analyzing an acoustic signal from the region of interest to indicate a mechanical or morphological property below the surface of the region.

* * * * *